US012636521B2

(12) United States Patent
Carlsson

(10) Patent No.: US 12,636,521 B2
(45) Date of Patent: May 26, 2026

(54) IMAGING SYSTEM FOR A RADIOTHERAPY DEVICE

(71) Applicant: Elekta Limited, Crawley (GB)

(72) Inventor: Per Carlsson, Crawley (GB)

(73) Assignee: Elekta Limited, Crawley (GB)

( * ) Notice: Subject to any disclaimer, the term of this patent is extended or adjusted under 35 U.S.C. 154(b) by 144 days.

(21) Appl. No.: 18/003,409

(22) PCT Filed: Jul. 1, 2021

(86) PCT No.: PCT/EP2021/068265
§ 371 (c)(1),
(2) Date: Dec. 27, 2022

(87) PCT Pub. No.: WO2022/003136
PCT Pub. Date: Jan. 6, 2022

(65) Prior Publication Data
US 2023/0263489 A1 Aug. 24, 2023

(30) Foreign Application Priority Data

Jul. 1, 2020 (GB) ....................................... 2010083

(51) Int. Cl.
*A61N 5/10* (2006.01)
*A61B 6/00* (2024.01)
(Continued)

(52) U.S. Cl.
CPC ............ *A61N 5/1049* (2013.01); *A61B 6/032* (2013.01); *A61B 6/06* (2013.01); *A61B 6/4078* (2013.01);
(Continued)

(58) Field of Classification Search
None
See application file for complete search history.

(56) References Cited

U.S. PATENT DOCUMENTS

2009/0283682 A1 11/2009 Star-lack et al.
2011/0096894 A1 4/2011 Uehara et al.
(Continued)

FOREIGN PATENT DOCUMENTS

WO WO-2010136911 A1 12/2010
WO WO-2013019583 A1 * 2/2013 ............. A61B 6/025

OTHER PUBLICATIONS

"International Application Serial No. PCT/EP2021/068265, International Search Report dated Sep. 29, 2021", (Sep. 29, 2021), 6 pgs.
(Continued)

*Primary Examiner* — Edwin C Gunberg

(74) *Attorney, Agent, or Firm* — Schwegman Lundberg & Woessner, P.A.

(57) ABSTRACT

Disclosed herein is an imaging system for a radiotherapy device which is configured to provide therapeutic radiation to a patient via a source of therapeutic radiation. The imaging system comprises a source of imaging radiation, a CBCT panel detector, and a CT detector, wherein the source of imaging radiation is configured to be adjustable such that in a first configuration it is configured to emit imaging radiation towards the CT detector and in a second configuration it is configured to emit imaging radiation towards the CBCT detector.

20 Claims, 5 Drawing Sheets

(51) Int. Cl.

| | |
|---|---|
| *A61B 6/03* | (2006.01) |
| *A61B 6/06* | (2006.01) |
| *A61B 6/40* | (2024.01) |
| *A61B 6/42* | (2024.01) |

(52) U.S. Cl.
CPC .......... *A61B 6/4085* (2013.01); *A61B 6/4233* (2013.01); *A61B 6/4266* (2013.01); *A61B 6/4452* (2013.01); *A61N 5/1077* (2013.01); *A61N 2005/1054* (2013.01); *A61N 2005/1061* (2013.01)

(56) References Cited

U.S. PATENT DOCUMENTS

| | | | |
|---|---|---|---|
| 2011/0211665 A1* | 9/2011 | Maurer, Jr. .......... | A61N 5/1039 378/19 |
| 2015/0131774 A1 | 5/2015 | Maurer, Jr. et al. | |

| | | |
|---|---|---|
| 2016/0081641 A1 | 3/2016 | Bouhnik et al. |
| 2017/0311910 A1 | 11/2017 | Inglese et al. |
| 2020/0121267 A1 | 4/2020 | Deutschmann |
| 2020/0170590 A1 | 6/2020 | Gagnon et al. |
| 2020/0171328 A1 | 6/2020 | Shea et al. |

OTHER PUBLICATIONS

"International Application Serial No. PCT/EP2021/068265, Written Opinion dated Sep. 29, 2021", (Sep. 29, 2021), 7 pgs.

"United Kingdom Application Serial No. 2010083.0, Examination Report dated Dec. 22, 2020", (Dec. 22, 2020), 5 pgs.

"European Application No. 21 742 070.0, Examination Report dated Mar. 7, 2025", (Mar. 7, 2025), 5 pgs.

"Chinese Application No. 202180049699.9, Office Action dated Sep. 26, 2025", w English Translation, (Sep. 26, 2025), 13 pgs.

"European Application No. 21 742 070.2, Office Action dated Apr. 22, 2026", Apr. 22, 2026, 8 pgs.

* cited by examiner

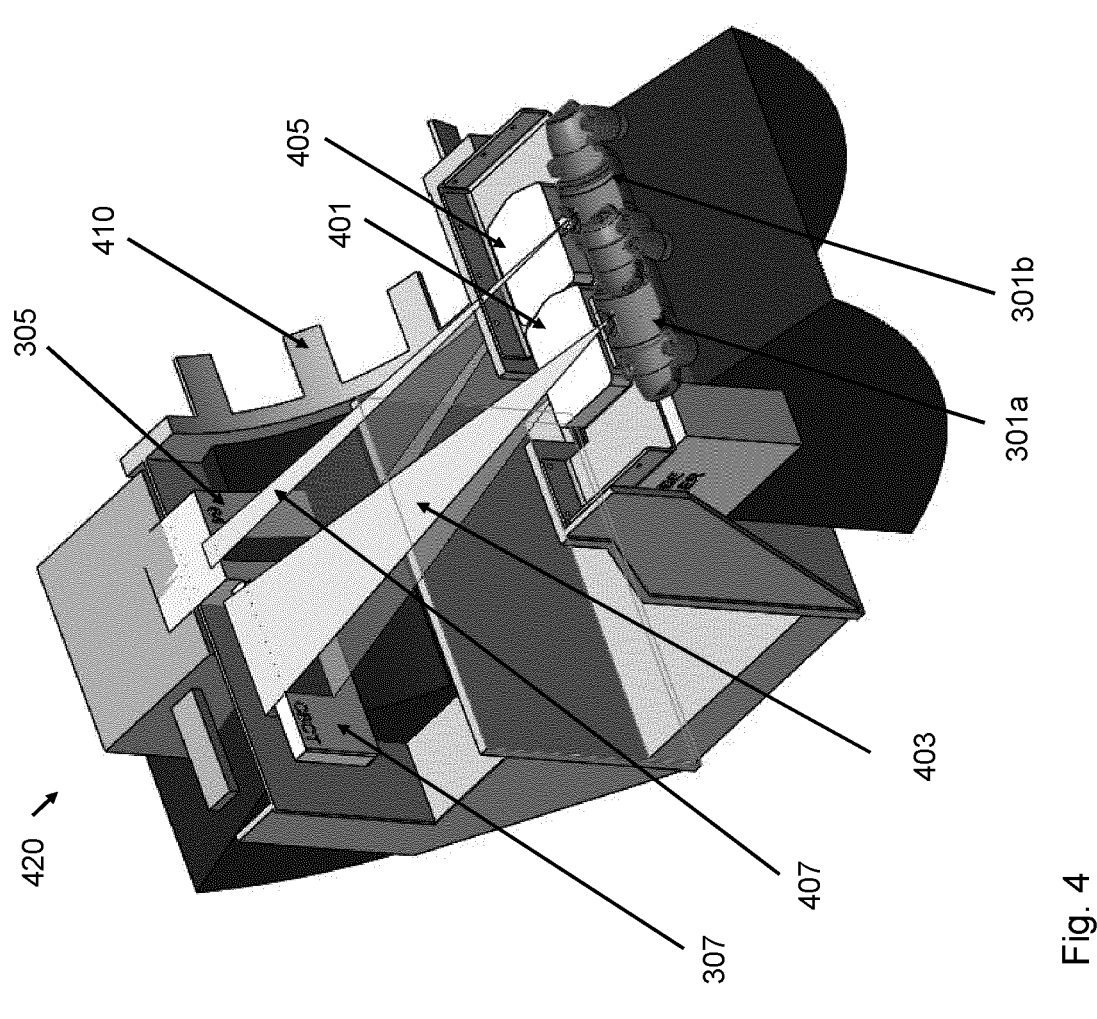
Fig. 4
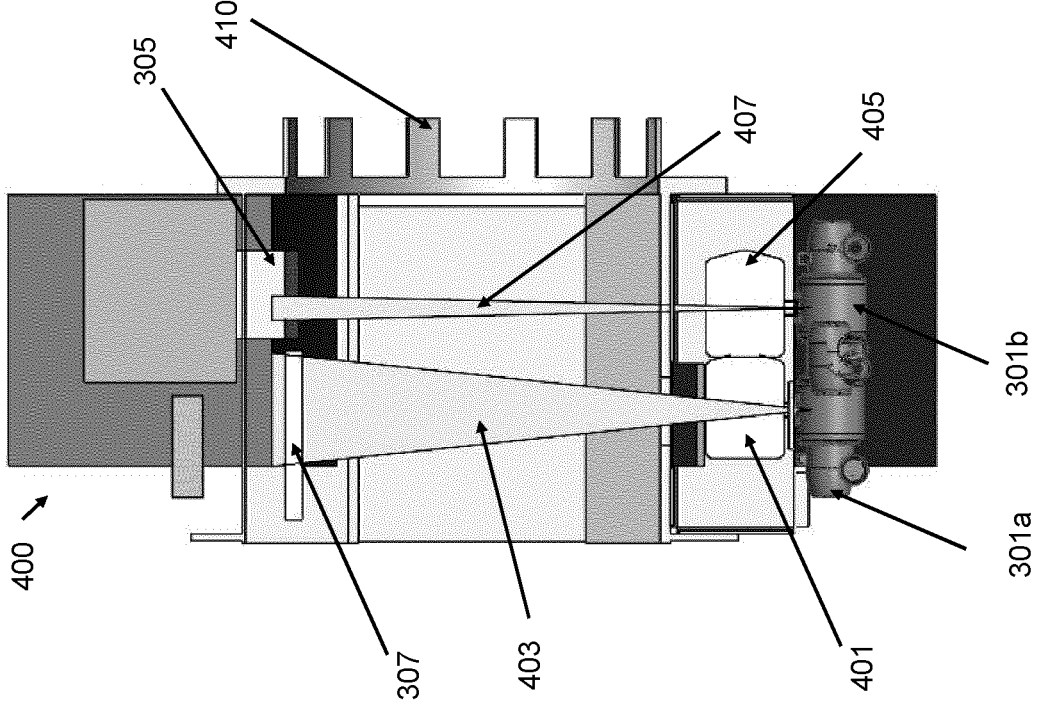

500

510 Acquire an image using a first detector panel of an imaging system before radiotherapy treatment 520 Update one or more radiation delivery variables based on the image 530 Deliver radiation according to the updated radiation delivery variables 540 Adjust source of imaging radiation and acquire an intrafraction image using a second detector panel

IMAGING SYSTEM FOR A RADIOTHERAPY DEVICE

PRIORITY APPLICATIONS

This application is a U.S. National Stage Filing under 35 U.S.C. § 371 from International Application No. PCT/EP2021/068265, filed on Jul. 1, 2021, and published as WO2022/003136 on Jan. 6, 2022, which claims the benefit of priority to United Kingdom Application No. 2010083.0, filed on Jul. 1, 2020; the benefit of priority of each of which is hereby claimed herein, and which applications and publication are hereby incorporated herein by reference in their entireties.

This disclosure relates to an imaging system for a radiotherapy device and methods therefor.

BACKGROUND

Radiotherapy can be described as the use of ionising radiation, such as X-rays, to treat a human or animal body. Radiotherapy is commonly used to treat tumours within the body of a patient or subject. In such treatments, ionising radiation is used to irradiate, and thus destroy or damage, cells which form part of the tumour. However, in order to apply a prescribed dose to a tumour or other target region within a subject, the radiation must pass through healthy tissue, irradiating and hence potentially damaging it in the process. It is a general aim of the field to minimise the dose received by healthy tissue during radiotherapy treatments.

Many different radiotherapy techniques exist, allowing radiation to be applied from different angles, at varying intensities, and for specific time periods. Before radiotherapy treatment, a radiation therapy treatment plan is created to determine how and where the radiation should be applied. Typically, such a treatment plan is created with the assistance of medical imaging technology. For example, a computed tomography (CT) scan may be taken of the patient in order to produce a three-dimensional image of the area to be treated. The three-dimensional image allows the treatment planner to observe and analyse the target region and identify surrounding tissues. In addition, the three-dimensional image can be recorded over a period of time, such as a breathing cycle, in order to provide a four-dimensional (4DCT) video that can inform the treatment plan.

Known imaging systems include CT imaging systems and cone beam computed tomography (CBCT) imaging systems. CT imaging systems have various advantages and disadvantages compared to CBCT imaging systems, with differences in quality, physical size, time of measurement, and cost.

There are many challenges involved with providing such systems as part of a radiotherapy device, including complexity and cost.

SUMMARY

An invention is set out in the independent claims. Optional features are set out in the dependent claims.

Embodiments will now be described, by way of example, with reference to the drawings of which:

FIG. 4 shows a cross-sectional view and a partial cutaway view of an imaging system according to the present disclosure coupled to a gantry;

OVERVIEW

Figure 1:
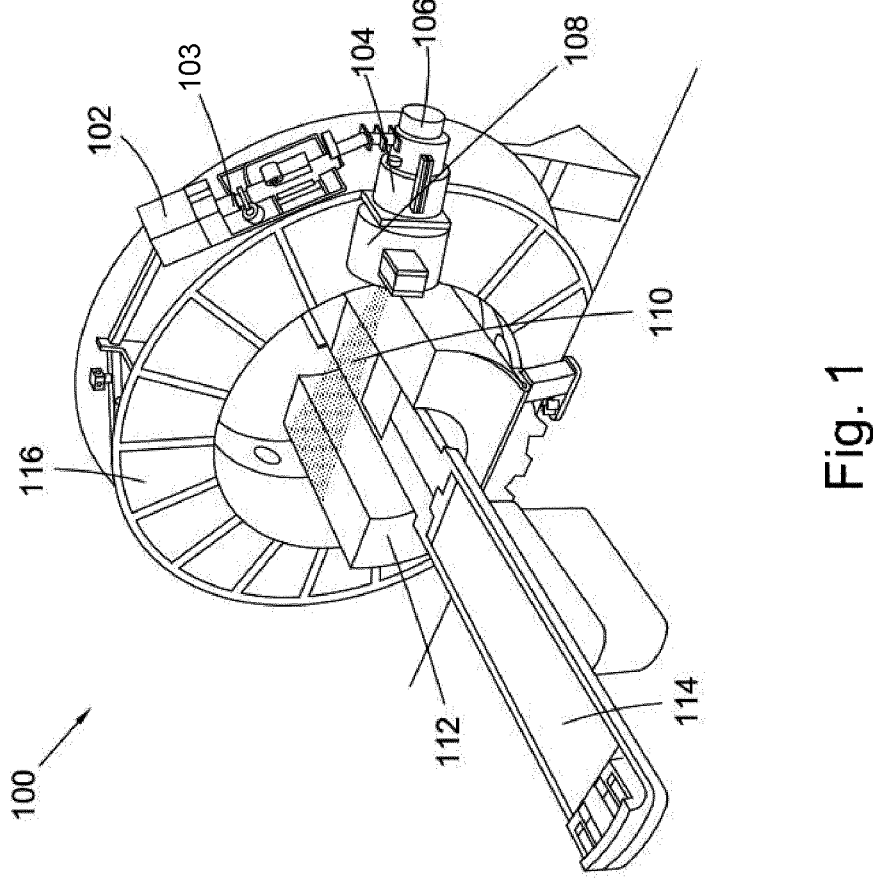
FIG. 1 shows a radiotherapy device or apparatus of known type.

In overview, the present disclosure relates to an imaging system for a radiotherapy device that can provide CT imaging capability and CBCT imaging capability. The imaging system comprises a single source of imaging radiation, a CT detector and a CBCT detector. The CT detector and CBCT detector are different types of detector with different characteristics. Embodiments are disclosed in which the single common source of imaging radiation can be used to provide alternate CT imaging capability and CBCT imaging capability.

As used herein, a CT imaging system is distinguished from a CBCT imaging system. These terms are used to refer to different imaging modalities and different associated imaging devices. CT imaging involves rotating a source of imaging radiation 360° around a patient at axially spaced positions with a fan beam directed towards a relatively narrow panel in order to acquire data which can be used to produce a 2D cross-sectional image of the patient. Either the source of imaging radiation, or the patient, can then be incrementally advanced in order to acquire another 2D image and thereby build up a 3D image of the patent or region of interest via multiple 360° rotations around the patient. Alternatively, rather than incremental advancements, the patient or source of radiation can be advanced slowly and continuously while the radiation source rotates, in order to acquire the necessary data to construct a 3D CT image via a spiral or helical delivery of imaging radiation. In a 'true' or 'traditional' CT imager, the imaging radiation is typically emitted in a thin 'fan' shape that projects an elongated shape that is much narrower in one direction than the other onto the detector. Hence a narrow, curved detector is used.

In contrast, a CBCT imaging system uses a broader, cone-shaped beam and larger panel in order to cover a large volume of the patient with a single full or half or other angle of rotation around the patient, thereby acquiring multiple 2D projections of the object from various angles used to reconstruct a 3D image, and CBCT systems are therefore able to provide 3D images quickly and with a reduced number of gantry rotations in comparison to traditional CT systems. For example, it is possible to achieve a 3D imaging volume via a single 180 degree rotation around a patient using a CBCT modality.

A CT detector is typically very expensive per unit area and so the surface area is minimised by using a curved detector that is translated around a patient. The curvature follows the geometry and angular spread of the fan beam and can have a comparatively narrow dimension transverse to the plane of the beam, i.e., of dimension comparable to the fan beam thickness. CBCT images are obtained using a normally less expensive two-dimensional flat panel detector that is not of sufficient quality to be used for CT imaging due to several technical differences and drawbacks. The CBCT images are typically quicker to obtain than CT images, and are typically used for intrafraction imaging. In part due to these advantages of cost and speed, CBCT imaging systems have been considered for use with radiotherapy devices, for example to provide 3D images which may guide or form the basis of radiation therapy.

However, CBCT images are typically lower quality and, unlike images produced by spiral delivery CT imaging, CBCT images contain inherent artefacts that need to be accounted for. Those disadvantages might compromise 3D image quality obtained by a CBCT system. There are other advantages achieved by using a thinner slice with spiral imaging in CT, such as that the scatter to the panel is reduced and, as mentioned above, the reconstruction process produces fewer artefacts—in general a higher image quality and lower dose to the patient can be obtained by CT imaging. However, a radiotherapy device comprising a 'true' or 'traditional' CT imaging system, capable of providing higher quality imaging than CBCT, is difficult to develop due to the cost and complexity of such a system. Even when trying to integrate a CT imaging system into a radiotherapy device, it is desirable to also include a CBCT-type imaging technique based on a two-dimensional panel, particularly for intrafraction imaging. However, producing such a large area panel with the quality required additionally for a CT imaging functionality is prohibitively expensive.

Accordingly, disclosed herein is an imaging system that can be integrated with a radiotherapy device in order to provide multiple types of imaging. The disclosure enables CT imaging and CBCT imaging to be integrated into a radiotherapy device without significant cost or complexity increase and with minimal change in the dimensions of the device.

Although this disclosure describes various examples and embodiments relating to CBCT imaging, it should be understood that the systems, devices, and methods disclosed herein may in fact be used to perform other types of cross-sectional imaging, including 2D imaging and 3D imaging. Accordingly, apparatus described as suitable for CBCT, such as detectors, should be interpreted as being suitable for the desired cone beam imaging technique, i.e. it may not be necessary for the detector to enable a full 3D sample to be produced and it may instead be designed to produce a 2D CBCT-type image. Similarly, variations of 3D and 4D CT imaging exist and the use of the term 'CT' should not be taken to be limiting to one particular variation of a 2D-slice or spiral configuration. The disclosure is intended to relate to a higher quality form of pre-treatment imaging, referred to as 'CT', and a lower quality, but faster, form of intrafraction imaging, referred to as 'CBCT'. Similarly, a 'flat panel' detector is disclosed for illustrative purposes and may, in some examples, be a curved detector that is suitable for two dimensional detection.

DETAILED DESCRIPTION

FIG. 1 shows a radiotherapy (RT) device 100. The device and its constituent components will be well known to the skilled person but is described here generally for the purpose of providing useful accompanying information for the present disclosure.

The RT device 100 shown in FIG. 1 comprises a source 102 of radiofrequency waves, RF transmission apparatus 103, an accelerating waveguide 104, a source of electrons 106, a treatment head including a collimator 108 such as a multi-leaf collimator used to shape a treatment beam 110, housing 112 (shown partially cut away), and a patient support surface 114. The depicted device does not have the usual housing which would cover the entire RT apparatus in a commercial setting such as a hospital. In use, the device would also comprise the housing which, together with the ring-shaped gantry, defines a bore. The patient support surface 114 is moveable and can be used to support a patient and move them, or another subject, into the bore when radiotherapy is to commence.

The RT apparatus beam generation system comprises the source 102 of radiofrequency waves, the accelerating waveguide 104, and the source of electrons 106. The beam generation system is configured to produce a beam of radiation, otherwise known as the treatment beam 110, that is collimated and shaped by the collimator 108 and directed towards the bore. The beam generation system is based on a linear accelerator (linac) design.

The source 102 of radiofrequency waves, such as a magnetron, is configured to produce radiofrequency waves. The source 102 of radiofrequency waves is coupled to the accelerating waveguide 104 via the RF transmission apparatus 103, which may include a circulator, and is configured to pulse radiofrequency waves into the accelerating waveguide 104. Radiofrequency waves may pass from the source 102 of radiofrequency waves through an RF input window and into an RF input connecting pipe or tube. The source of electrons 106, such as a diode or triode electron gun, is also coupled to the accelerating waveguide 104 and is configured to inject electrons into the waveguide 104. The injection of electrons into the accelerating waveguide 104 is synchronised with the pumping of the radiofrequency waves into the accelerating waveguide 104. The design and operation of the source 102 of radiofrequency waves, source of electrons 106, and the accelerating waveguide 104 is such that the radiofrequency waves accelerate the electrons to very high energies as the electrons propagate through the accelerating waveguide 104.

The design of the accelerating waveguide 104 depends on whether the accelerating waveguide 104 accelerates the electrons using a standing wave or travelling wave, though the waveguide typically comprises a series of cells, each cell connected by a hole or 'iris' through which the electron beam may pass. The cells are coupled in order that a suitable electric field pattern is produced which accelerates electrons propagating through the accelerating waveguide 104. As the electrons are accelerated in the accelerating waveguide 104, the electron beam path may be controlled by a suitable arrangement of steering magnets, or steering coils, which surround the accelerating waveguide 104. The arrangement of steering magnets may comprise, for example, two sets of quadrupole magnets.

Once the electrons have been accelerated, they may pass into a flight tube. The flight tube may be connected to the waveguide by a connecting tube. This connecting tube or connecting structure may be called a drift tube. The electrons travel toward a heavy metal target which may comprise, for example, tungsten. Whilst the electrons travel through the flight tube, an arrangement of focusing magnets act to direct and focus the beam on the target.

To ensure that propagation of the electrons is not impeded as the electron beam travels toward the target, the accelerating waveguide 104 is evacuated using a vacuum system comprising a vacuum pump or an arrangement of vacuum pumps. The pump system is capable of producing ultra-high vacuum (UHV) conditions in the accelerating waveguide 104. The vacuum system also ensures UHV conditions in the source of electrons 106 and, if used, the drift tube and flight tube. Electrons can be accelerated to speeds approaching the speed of light in the evacuated waveguide.

The beam generation system is configured to direct the treatment beam 110 toward a patient positioned on the patient support surface 114. The treatment beam 110 comprises therapeutic radiation. The beam generation system may comprise a heavy metal target toward which the high energy electrons exiting the waveguide are directed. When the electrons strike the target, X-rays are produced in a variety of directions. A primary collimator may block X-rays travelling in certain directions and pass only forward travelling X-rays to produce the treatment beam 110. The X-rays may be filtered and may pass through one or more ion chambers for dose measuring. The beam can be shaped in various ways by beam-shaping apparatus, for example by using the collimator 108, before it passes into the patient as part of radiotherapy treatment.

In some implementations, the beam generation system is configured to emit either an X-ray beam or an electron particle beam. Such implementations allow the device to provide electron beam therapy, i.e. a type of external beam therapy where electrons, rather than X-rays, are directed toward the target region. It is possible to 'swap' between a first mode in which X-rays are emitted and a second mode in which electrons are emitted by adjusting the components of the beam generation system. In essence, it is possible to swap between the first and second mode by moving the heavy metal target in or out of the electron beam path and replacing it with a so-called 'electron window'. The electron window is substantially transparent to electrons and allows electrons to exit the flight tube.

Typically, a radiation detector is positioned diametrically opposed to the collimator 108. The radiation detector is suitable for, and configured to, produce radiation intensity data. In particular, the radiation detector is positioned and configured to detect the intensity of radiation which has passed through the subject. The radiation detector may form part of a portal imaging system.

The beam generation system is attached to the rotatable gantry 116 so as to rotate with the gantry 116. In this way, the beam generation system is rotatable around the patient so that the treatment beam 110 can be applied from different angles around the gantry 116. In a preferred implementation, the gantry is continuously rotatable. In other words, the gantry can be rotated by 360 degrees around the patient, and in fact may continue to be rotated past 360 degrees. The gantry may be ring-shaped, i.e. a ring-gantry.

The RT device 100 of FIG. 1 may be controlled by a controller (not shown). The controller is a computer, processor, or other processing apparatus. The controller may be formed by several discrete processors; for example, an RT apparatus processor, which controls the operation of the RT apparatus; and a subject support surface processor which controls the operation and actuation of the patient support surface 114. The controller is communicatively coupled to a memory, e.g. a computer readable medium.

Figures 2A, 2B:
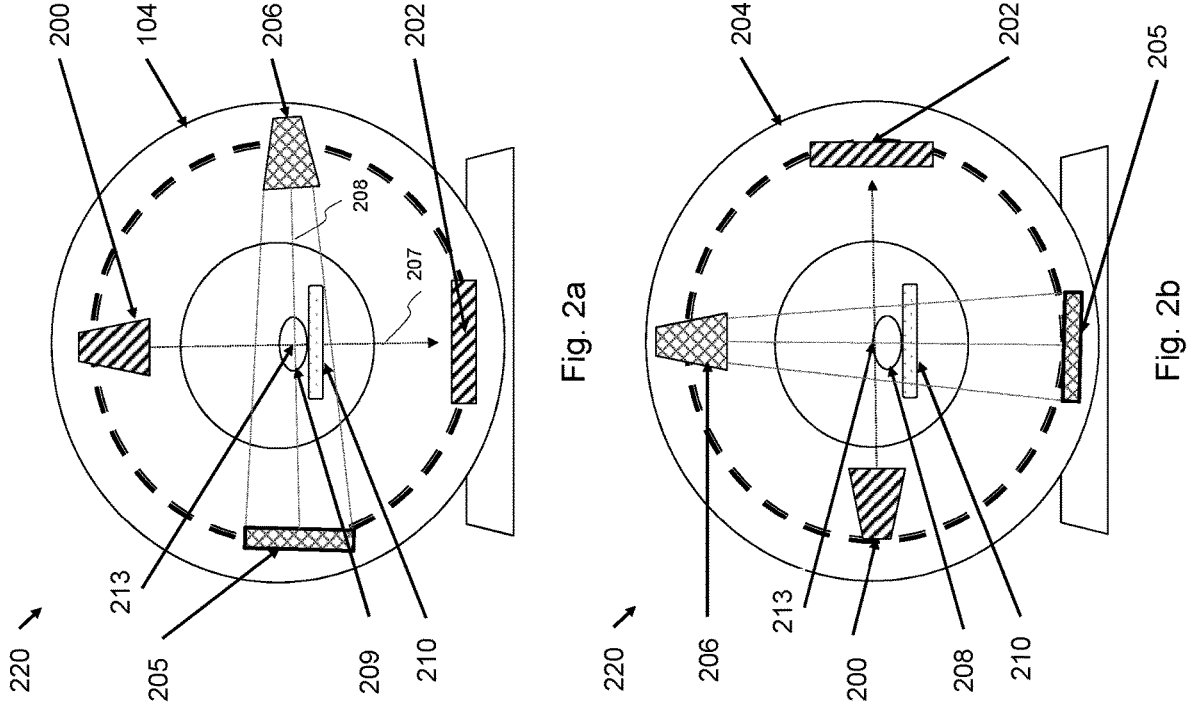
FIG. 2a shows a cross-sectional view of a radiotherapy device or apparatus of known type with an imaging system.
FIG. 2b shows a cross-sectional view of a radiotherapy device or apparatus of known type with an imaging system.

FIG. 2a and FIG. 2b show a possible geometrical arrangement of a radiotherapy device 220, which may be the radiotherapy device 100 of FIG. 1, that additionally comprises an imaging system of known type. The imaging system comprises a source of imaging radiation 206, such as a source of X-ray radiation, and an imaging detector 205. The device 220 depicted in FIGS. 2a and 2b is configured to provide radiotherapy treatment in a co-planar arrangement. The imaging system and source of therapeutic radiation 200 are coupled to a gantry 204, which may be a ring gantry. The source of therapeutic radiation 200 is configured to emit radiation along a therapeutic radiation axis 207 to a radiation detector 202 and the source of imaging radiation 206 is configured to emit radiation along an imaging beam axis 208.

The source of therapeutic radiation 200 is rotatable around a patient 209 positioned in a treatment volume of the device 220. The point in space through which the therapeutic radiation axis 207 passes regardless of gantry rotation angle is the radiation isocentre 213. In other words, radiation may be delivered to a radiation isocentre 213 at the centre of the gantry 204 regardless of the angle to which the radiation head 200 is rotated around the gantry 204. The rotation axis of the gantry 204 may also pass through the radiation isocentre 213, in a direction which is perpendicular to both the therapeutic radiation axis 207 and the imaging radiation axis 208. In the co-planar arrangement depicted in FIGS. 2a and 2b, radiation is emitted in a plane which is perpendicular to the axis of rotation of the radiation source 200.

The device 220 may comprise a moveable patient table 210 which is configured to move the patient 213 into, and out from, the bore of the gantry 204. The patient table 210 may be moveable by a suitable arrangement or configuration of motors and actuators. To provide an image of the patient 213, the patient table 213 is actuated to move the patient into the bore of the gantry. While at least a portion of the patient 213 is inside the bore, the imaging system rotates around the patient while the source of imaging radiation 206 emits a beam of radiation. Radiation intensity data is collected by the detector 205, which is indicative of the degree to which the imaging radiation has been attenuated by the patient 213.

As the radiation is delivered to the patient, for example according to a treatment plan, the gantry 204 rotates causing the radiation detector 202 and source of therapeutic radiation 200 to rotate together around the circular support track 206 such that they are always arranged 180 degrees from one another around the gantry 204. The source of therapeutic radiation 200 thus directs radiation toward the patient 209 from various angles around the patient 209. In FIG. 2a, the source of therapeutic radiation 200 is at the top of the gantry 204 and the radiation detector 202 is at the bottom of the gantry 204. FIG. 2b shows both components having been rotated 180 degrees about the gantry rotation axis, which is into the plane of the diagram.

The components of the imaging system and the radiotherapy system can be rigidly coupled to the gantry 204 so as to retain a fixed angle which can be 90 degrees or another value between each component as the gantry 204 is rotated. In FIG. 2a, the source 206 of imaging radiation is at the right-hand side of the gantry 204 and the imaging radiation detector 205 is at the left-hand side of the gantry 204. FIG. 2b shows both components having been rotated 180 degrees about the gantry rotation axis. The angle between the therapeutic radiation beam axis and imaging radiation axis is constant and independent of the rotation of the gantry.

The geometry of FIG. 2a and FIG. 2b may be used alternatively for either CT imaging or CBCT imaging. For CT imaging, an appropriate CT imaging detector and CT source of imaging radiation are used. FIG. 2a and FIG. 2b show a fan beam of imaging radiation, as would be used for CT imaging. In that case, the source of imaging radiation 206 is configured to emit a fan-shaped beam which nonetheless has a central axis which is depicted in the figures as a dashed line. For CBCT imaging, a respective CBCT imaging radiation detector and source of imaging radiation are used. In that case, the source of imaging radiation 206 is configured to emit a cone-shaped beam. The gantry can be rotated such that the source of imaging radiation 206 and the imaging radiation detector 205 rotate about the patient according to the position and speed requirements necessary to produce the desired image. As the imaging system is rotated and attenuation data is gathered, data from different angles is collected which allows the reconstruction of a cross-sectional image using known techniques. The imaging system may also comprise a processor, or controller, configured to receive the signals from each of the detector and produce, or reconstruct, an image based on the signals.

Figures 3A, 3B:
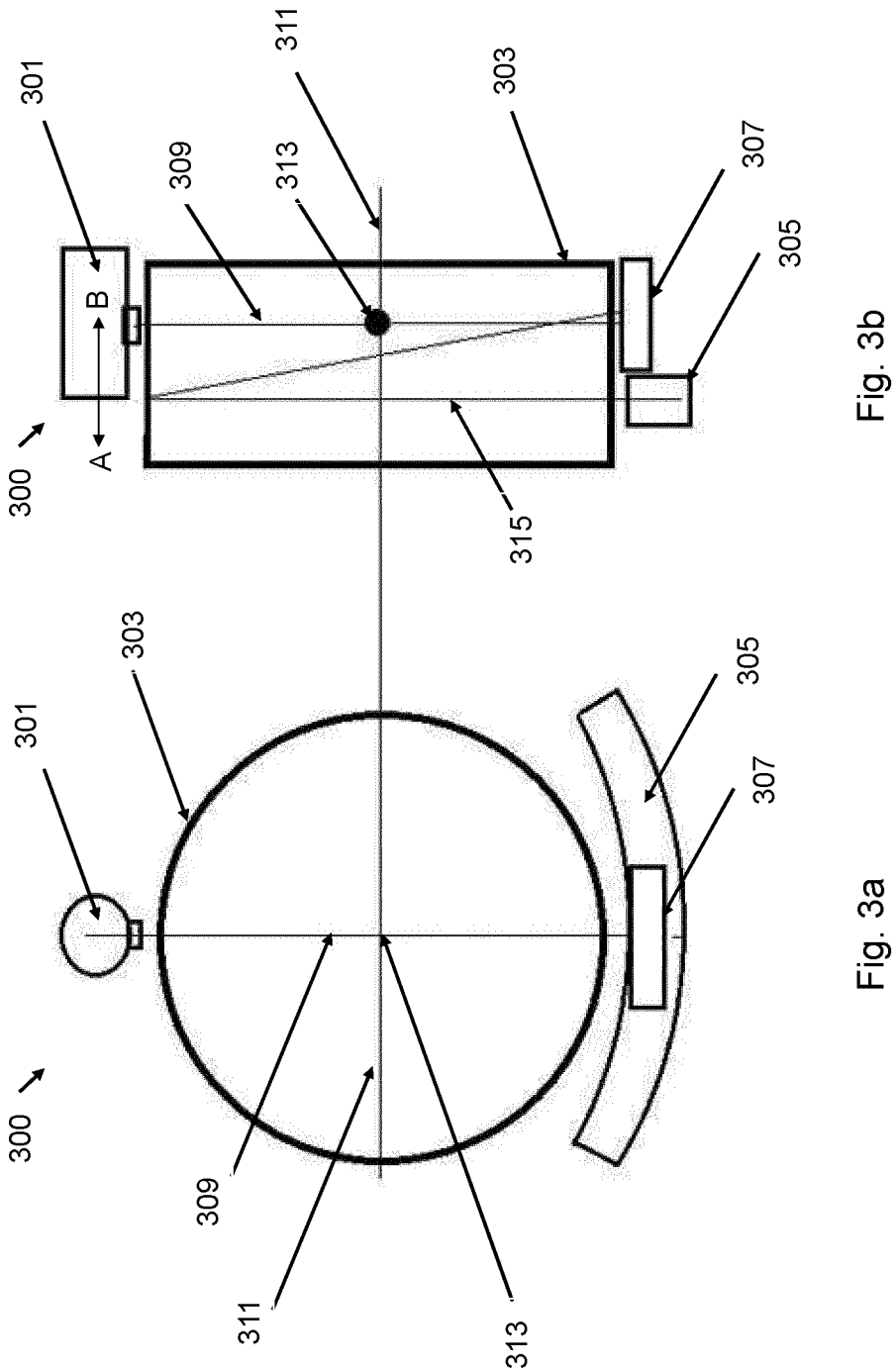
FIG. 3a shows a cross-sectional view of an imaging system geometry according to the present disclosure.
FIG. 3b shows a cross-sectional view of an imaging system geometry according to the present disclosure.

FIG. 3 shows an example imaging system that improves upon the arrangement of FIG. 2a and FIG. 2b in order to incorporate CT imaging and CBCT imaging capability within one system, rather than having to limit a system to one particular type of imaging due to cost and complexity constraints. The system is shown in front elevation 300, corresponding to the view in FIG. 2 and a side elevation 320. A source 301 of imaging radiation is mounted to a rotatable ring-shaped gantry 303, such as the gantry of the radiotherapy device of FIG. 1. A patient or subject that is to undergo imaging or radiotherapy can be placed within the bore defined by the gantry 303.

Two detectors are mounted to the ring-shaped gantry 303 on the opposite side to the source 301 of imaging radiation. A first, curved detector 305 is of a nature and quality suitable for CT imaging. For example, the curved detector may be a solid-state detector comprising a scintillator and/or photo-detector. The curved detector 305 is curved, with the axis of curvature being the same as the axis of curvature of the gantry, although the degree of curvature may not be the same. The curved detector 305 has a slim, elongated face that provides coverage for a length equivalent to the lateral body width of a patient in the direction of which a cross-sectional image is to be obtained (in one example, the standard length of 80 cm is used). The width of the face of the curved detector 305 does not extend further than is necessary in order to provide measurements suitable for CT imaging, reducing the total detector surface area required. The system can enable CT imaging while utilising an existing radiotherapy device gantry that can rotate for example at 20 rpm, or even faster, without requiring modification to the gantry structure or driving technique, producing very high cost efficiency.

A second, flat panel detector 307 is of a quality suitable for CBCT, typically ideal for 2D imaging with high resolution but with less sensitivity, dynamic range and slower readout frequency, i.e. of lower image quality and lower expense than the curved detector 305. For example, the flat panel detector 307 may be an amorphous silicon based detector. The flat panel detector 307 is differently shaped to the curved detector 305 and is a planar/non-curved panel with a width and length that are more similar in size to each other and less elongated than the curved detector 305, and may in fact produce a square shaped detector.

The source 301 of imaging radiation is configured to emit radiation in a direction parallel to an imaging axis 309 in the direction of the panels. The imaging axis 309 intersects perpendicularly with a second axis, a radiotherapy axis 311 that defines the direction of therapeutic radiation for a radiotherapy device as in FIG. 1 and FIGS. 2a and 2b. The two axes intersect at an isocentre 313. In the side perspective 320, the source 301 of imaging radiation is shown as being positioned diametrically opposite the flat panel detector 307, along the imaging axis 309. The flat panel detector 307 is hence placed in alignment with the isocentre 313. The flat panel detector 307 comprises a flat panel of sufficient size (such as 20×20 cm, 25×25 cm, 40×40 cm, or any other suitable size) for 2D imaging, and has the same rotation angle as the curved detector 305. In such a configuration, with the source 301 of imaging radiation in a first position, the source 301 of imaging radiation and the flat panel detector 307 are able to be rotated about the patient in order to provide CBCT imaging. Imaging radiation from the source 301 of imaging radiation is emitted along the imaging axis 309 and, in the configuration shown, is incident on the second detector 307 but not the curved detector 305. The curved detector 305 is placed slightly outside the isocentre 313 in the longitudinal direction, although with the same rotation angle as the isocentre 313. As shown in FIG. 3, the curved detector 305 is placed adjacent to the flat panel detector 307, and thus adjacent to the imaging axis 309. The placement may be of a distance equivalent to 32, or 64, or more, lines away from the imaging axis 309 passing through the isocentre 313. A line will be understood by those skilled in the art to be equivalent to a pixel, such as a 1 mm wide pixel.

The detectors are sized such that their placement side by side, or adjacent to one another, advantageously does not extend the length of the bore of the radiotherapy device, which is determined by other parts and components of the gantry. Thus, respective detection capability suitable for CT imaging with the curved detector 305 and CBCT imaging with the flat panel detector 307 can be achieved without unduly increasing the size or footprint of the radiotherapy device.

In an example, the dimensions of the curved detector 305 are 800 mm×64 mm, although any suitable size may be used.

The source of imaging radiation can be configured to be adjustable such that in a first configuration it is configured to emit imaging radiation towards a CT detector, and in a second configuration it is configured to emit imaging radiation towards a CBCT panel detector. Such a source of imaging radiation may be the source of imaging radiation described with respect to any imaging system disclosed herein. The source 301 of imaging radiation is configured such that it can alternate between illuminating the flat panel detector 307, as shown in FIG. 3, and illuminating the curved detector 305. In one example, the source 301 of imaging radiation is movable, or translatable, using a motor, such that it can be moved laterally and directed to emit along a second imaging axis 315, rather than the previous imaging axis 309. The arrow A-B in FIG. 3 indicates a direction of possible linear motion of the source 301 of imaging radiation. In another example, the source 301 of imaging radiation can be angularly rotated, or tilted, to point towards and illuminate the curved detector 305 such that the curved detector 305 is illuminated by imaging radiation in the tilted position rather than the flat panel detector 307. In that case the curved detector 305 can be placed at a tilted angle such that the illumination axis remains orthogonal, however, it need not necessarily be placed as such and may in fact be placed such that the illumination axis is not orthogonal to the detector surface. Of course, the default position can be reversed such that the source 301 of imaging radiation must be tilted towards the flat panel 307 which may once again be mounted in a corresponding angled or tilted position. In each example, the subject or patient to be imaged is placed between the source 301 of imaging radiation and the respective detector, and the source 301 of imaging radiation and respective detector is rotated about the subject according to the requirements of a CT imaging technique (using the curve detector 305) or a CBCT imaging technique (using the flat panel detector 307).

The imaging coordinate systems of the respective CBCT and CT imaging are very accurately calibrated with reference to the radiation isocentre 313. Hence the images acquired and the 3D volumes reconstructed can be related to the radiation isocentre 313 so that the patient offset can be calculated and compensated for.

In some examples, the source 301 of imaging radiation is configured to move such that two alternative collimators can be used. Alternatively, a single adjustable collimator is used. The purpose of each collimator component is to shape the beam appropriately for the respective technique of CT or CBCT, i.e. a fan-beam of imaging radiation is produced for a CT technique using the curved detector 305, and a cone beam of imaging radiation is produced for a CBCT technique using the flat panel detector 307. In one example, rather than moving the source 301 of imaging radiation either laterally or angularly, the source 301 of imaging radiation emits a wide enough cone or fan beam that both detector panels are illuminated by it. In such an example, collimation may be selectively applied such that a cone beam is incident on the second detector 307 for CBCT and a fan beam is incident on the first detector 305 for CT. Such an approach is dependent upon enough flux density being provided by the wider beam that each detector can obtain adequate signal.

In some examples, the source 301 of imaging radiation is an x-ray tube and generator suitable for CT imaging, although other forms of imaging radiation may be used. Using the same source for two types of imaging beneficially allows both types of imaging to be integrated into a radiotherapy system without undue cost and complexity. CT imaging can be used for pre-treatment imaging and CBCT, or 2D, imaging can be used for intrafraction imaging. When using an x-ray tube and generator, the generator is configured such that the source 301 of imaging radiation can be operated either in a pulsed manner or in a continuous manner. In either pulsed or continuous operation, the source may illuminate either one panel at a time, or both panels simultaneously, depending upon the arrangement and method chosen from those disclosed herein. The source may operate at a typical energy of between 50 to 150 kV but may also operate outside of that range, or at more than one energy.

In some examples, the source 301 of imaging radiation is selected and positioned so that its field of view barely projects onto the full flat panel surface of the flat panel detector 305, in other words, such that the flat panel detector 305 substantially fills the imaging source field of view. A control system of the source 301 of imaging radiation is configured so that the source can operate in a pulsed manner and/or can operate in a manner suitable for fluoroscopy, with continuous beams of imaging radiation.

FIG. 4 shows a cross-section 400 and a partial cut away 420 of a system using the geometry of FIG. 3. The source 301 of imaging radiation is shown in each depiction as being present in two alternate positions, however, this is for illustration purposes only. As described above, only one source of imaging radiation is used and in the system of FIG. 4 the source 301 of imaging radiation is moveable from a first position 301*a*, in which the source passes through a first collimator 401 that produces a cone beam 403 and is directed to a flat panel detector suitable for CBCT, equivalent to the flat panel detector 307 of FIG. 3. In the second position 301*b*, the source 301 of imaging radiation passes through a second collimator 405 that produces a fan beam 407 and is directed to the CT detector, which is equivalent to the curved detector 305 of FIG. 3. Alternatively, a single collimator component may be used that is adjustable such that it either produces a fan beam or a cone beam. In each example, the fan beam has a cross section much narrower in one dimension that the other, and the cone beam has a cross section that has two similar dimensions, and may be approximately circular or square. The components are mounted on a rotatable gantry 410, as in the system of FIG. 3. The system of FIG. 4 may, like the system of FIG. 3, be used with the radiotherapy device 100 of FIG. 1. The difference in shape and projection shape between the narrow fan beam 407 and the broader cone beam 403 is shown in FIG. 4.

Figure 5:
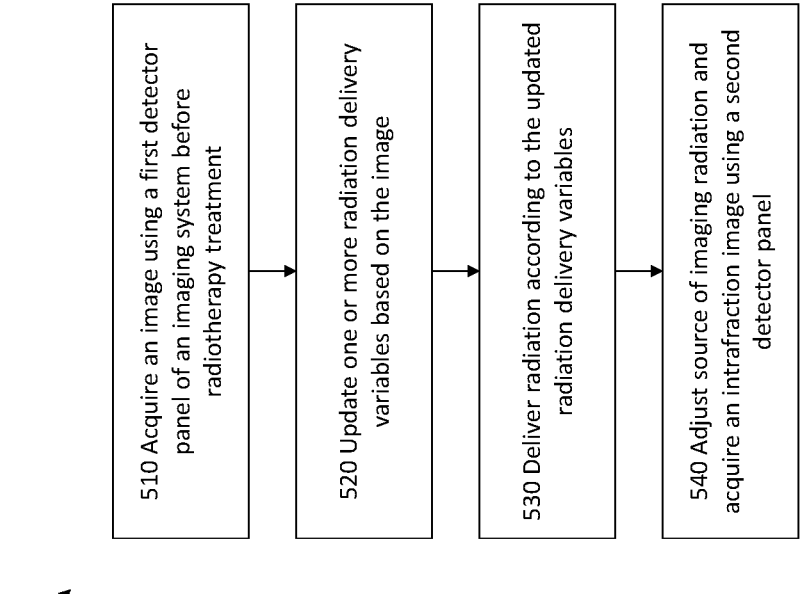
FIG. 5 shows steps performed in a method for radiotherapy imaging according to the present disclosure.

FIG. 5 is a flowchart depicting a method 500 according to the present disclosure. The method 500 may be performed using either of the systems depicted in FIG. 3 or FIG. 4. The method 500 is an example of the improved imaging options allowed by the systems of the present disclosure.

In overview, the method 500 may be used to update an existing treatment plan during delivery of the plan, i.e. during the radiotherapy treatment. An image taken by an imaging system at a particular gantry rotation angle and along a particular 'line of sight' can be used to inform the delivery of radiation along the same line of sight.

In an example, an existing treatment plan may be comprised of a set of several radiation delivery variables which have been determined for each of a plurality of gantry rotation angles. Clinical equivalent CT images can be taken and a 3D tomographic volume reconstructed. The original plan can thus be checked against the actual anatomy of the patient and, if needed, the plan can be updated or adapted so that the plan and dose to be delivered will accurately hit the target from all angles. Alternatively, the position of the patient can be adjusted in 3D or in 6D according to the CT image(s). Such pre-treatment imaging can be performed using the CT imaging capability of the system.

At step 510, an image is acquired using a first detector panel. In an implementation, the imaging system is a CT imaging system and the image is a CT image. The first detector panel is suitable for CT imaging, such as the curved detector 305 of FIG. 3.

As described above, the source of imaging radiation is movable laterally, or rotatable, or produces a sufficiently wide beam, such that it can illuminate two adjacent detectors. At step 510, the source of imaging radiation is positioned such that it can illuminate the first detector panel.

At step 520, one or more radiation delivery variables are updated based on the acquired image. This can be done in any appropriate manner as will be apparent to the skilled reader. For example, the radiation delivery variables may include one or more beam weights. The radiation delivery variables may also include beam collimation variables, which may relate to the shape and size of the beam. Beam collimation variables may include, for example, the position of one or more leaves of a multi-leaf collimator (MLC), the position of a beam blocker or beam diaphragm, and/or the degree of tilt or the position of a beam blocker and/or MLC. The radiation delivery variables may also include the length of time for which radiation is delivered. The radiation delivery variables may also include a gating variable, which determine whether or not the beam is gated, i.e. halted.

In an example, the CT image shows that target region has changed position relative to the images which were used to form the basis of the original treatment plan. This may be because the patient has adjusted their position on the support surface. The radiation delivery variables can be updated to account for this change. For example, the MLC leaf positions may be adjusted, either systematically or individually, in order that the desired dose distribution is achieved, the patient positioning system can be adjusted in 3D or in 6D or the treatment plan can be updated-all to achieve target coverage and spare healthy tissue. The update can be performed using known optimisation techniques which are known to the skilled person.

At step 530, the gantry is rotated so that the therapeutic radiation beam axis aligns with the imaging beam axis at the time the image was acquired at point 520. In other words, the image is acquired at a first time along a first axis. The gantry is rotated by the necessary angle until, at a second time, the radiation beam axis aligns with the first axis such that the source of therapeutic radiation can deliver radiation along the first axis.

At step 540, radiation is delivered according to the updated radiation delivery variable. The source of imaging radiation is adjusted, either by changing its angle or tilt, or moving it laterally, or adjusting a collimator, such that it is able to illuminate a second detector panel. The second detector panel is suitable for 2D or CBCT imaging, such as the flat panel 307 of FIG. 3, and is used to perform intrafraction imaging. Typically the CBCT panel and coordinate system is aligned with the radiation iso centre so that 2D images can be acquired with the patient in the same position during an irradiation sequence, even if the pulses are interlaced to enable best image quality, A computer-based system may be used for controlling or operating various parts of the systems, devices, methods and apparatuses disclosed herein. The computer-based system can be implemented in software, firmware and/or hardware and may comprise a computer-readable medium containing instructions that, when executed by a processor, cause the system to perform any of the methods described herein.

It is to be understood that the above description is intended to be illustrative, and not restrictive. Many other implementations will be apparent to those of skill in the art upon reading and understanding the above description. Although the present disclosure has been described with reference to specific example implementations, it will be recognized that the disclosure is not limited to the implementations described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

The invention claimed is:

1. An imaging system for a radiotherapy device configured to provide therapeutic radiation to a patient via a source of therapeutic radiation, the imaging system comprising:
   a source of imaging radiation;
   a cone beam computed tomography (CBCT) panel detector; and
   a computed tomography (CT) detector;
   wherein the source of imaging radiation is configured to be adjustable such that in a first configuration the source of imaging radiation is configured to emit imaging radiation towards the CT detector and in a second configuration it is configured to emit imaging radiation towards the CBCT detector, wherein, in the second configuration, the source of imaging radiation is configured to emit imaging radiation along a first imaging axis, and the CT detector is positioned adjacent to the first imaging axis.

2. The imaging system of claim 1, wherein the source of imaging radiation is configured to move between a first position and a second position, and wherein the first position corresponds to the first configuration and the second position corresponds to the second configuration.

3. The imaging system of claim 2, wherein the source of imaging radiation is configured to move between the first position and second position through a translation mechanism.

4. The imaging system of claim 2, wherein the source of imaging radiation is configured to move between the first position and second position through a rotation mechanism.

5. The imaging system of claim 1, further comprising:
   a collimator component, arranged such that, when the source of imaging radiation is in the first configuration, the collimator component is configured to shape radiation into a fan beam, and when the source of imaging radiation is in the second configuration, the collimator component is configured to shape radiation into a cone beam.

6. The imaging system of claim 1, wherein the imaging radiation is X-ray radiation.

7. The imaging system of claim 1, wherein the source of imaging radiation is configured to operate in a pulsed manner.

8. The imaging system of claim 1, wherein the dimensions of the CT detector are 800 mm×64 mm.

9. The imaging system of claim 1, wherein the dimensions of the CBCT panel detector are 250×250 mm.

10. A radiotherapy device comprising:
   an imaging system, wherein the radiotherapy device is configured to provide therapeutic radiation to a patient via a source of therapeutic radiation, and wherein the imaging system comprises:
   a source of imaging radiation;
   a cone beam computed tomography (CBCT) panel detector; and
   a computed tomography (CT) detector, wherein the source of imaging radiation is configured to be adjustable such that in a first configuration it is configured to emit imaging radiation towards the CT detector and in a second configuration it is configured to emit imaging radiation towards the CBCT detector, wherein, in the second configuration, the source of imaging radiation is configured to emit imaging radiation along a first imaging axis, and the CT detector is positioned adjacent to the first imaging axis.

11. The radiotherapy device of claim 10, wherein the imaging system comprises:
   a collimator component, arranged such that, when the source of imaging radiation is in the first configuration, the collimator component is configured to shape radiation into a fan beam, and when the source of imaging radiation is in the second configuration, the collimator component is configured to shape radiation into a cone beam.

12. The radiotherapy device of claim 10, wherein the source of imaging radiation is configured to move between a first position and a second position, wherein the first position corresponds to the first configuration and the second position corresponds to the second configuration, and wherein the source of imaging radiation is configured move between the first position and second position using at least one of a translation mechanism or a rotation mechanism.

13. A method for imaging for radiotherapy, the method comprising:
   acquiring an image using a source of imaging radiation in a first configuration and a Computed Tomography (CT) detector panel prior to radiotherapy treatment;

updating one or more radiation delivery variables based on the image;

configuring a radiotherapy device to deliver treatment according to the updated radiation delivery variables, adjusting the source of imaging radiation to a second configuration wherein, in the second configuration, the source of imaging radiation is configured to emit imaging radiation along a first imaging axis, and the CT detector panel is positioned adjacent to the first imaging axis; and acquiring a second image using the source of imaging radiation in the second configuration and a Cone Beam Computed Tomography (CBCT) detector panel.

14. The method of claim 13, comprising:

moving the source of imaging radiation between a first position and a second position, wherein the first position corresponds to the first configuration and the second position corresponds to the second configuration.

15. The method of claim 14, wherein the source of imaging radiation is configured to move between the first position and second position through a translation mechanism.

16. The method of claim 14, wherein the source of imaging radiation is configured to move between the first position and second position through a rotation mechanism.

17. The method of claim 13, wherein the imaging radiation is X-ray radiation.

18. A non-transitory computer-readable medium containing instructions that, when executed by a processor, cause the processor to perform operations comprising:

acquiring an image using a source of imaging radiation in a first configuration and a Computed Tomography (CT) detector panel prior to radiotherapy treatment;

updating one or more radiation delivery variables based on the image;

configuring a radiotherapy device to deliver treatment according to the updated radiation delivery variables;

adjusting the source of imaging radiation to a second configuration wherein, in the second configuration, the source of imaging radiation is configured to emit imaging radiation along a first imaging axis, and the CT detector panel is positioned adjacent to the first imaging axis; and acquiring a second image using the source of imaging radiation in the second configuration and a Cone Beam Computed Tomography (CBCT) detector panel.

19. The non-transitory computer-readable medium of claim 18, the operations comprising:

moving the source of imaging radiation between a first position and a second position, wherein the first position corresponds to the first configuration and the second position corresponds to the second configuration.

20. The non-transitory computer-readable medium of claim 19, wherein the source of imaging radiation is configured to move between the first position and second position through a translation mechanism.

* * * * *